(12) United States Patent
Olah et al.

(10) Patent No.: US 10,893,370 B1
(45) Date of Patent: Jan. 12, 2021

(54) SYSTEM AND METHOD FOR AIDING HEARING

(71) Applicant: Texas Institute of Science, Inc., Richardson, TX (US)

(72) Inventors: Laslo Olah, Richardson, TX (US); Grigorii Sokolovskii, St. Petersburg (RU); Sergey Losev, St. Petersburg (RU); Ekaterina Sokolovskaya, The Hague (NL); Peter Czifra, Budapest (HU); Gergely Sebestyen, Budapest (HU)

(73) Assignee: Texas Institute of Science, Inc., Richardson, TX (US)

( * ) Notice: Subject to any disclaimer, the term of this patent is extended or adjusted under 35 U.S.C. 154(b) by 0 days.

(21) Appl. No.: 17/029,209

(22) Filed: Sep. 23, 2020

Related U.S. Application Data

(63) Continuation-in-part of application No. 17/026,955, filed on Sep. 21, 2020, which is a continuation-in-part of application No. 16/959,972, filed as application No. PCT/US2019/012550 on Jan. 7, 2019.

(60) Provisional application No. 62/935,961, filed on Nov. 15, 2019, provisional application No. 62/904,616, filed on Sep. 23, 2019, provisional application No. 62/613,804, filed on Jan. 5, 2018.

(51) Int. Cl.
*H04R 25/00* (2006.01)

(52) U.S. Cl.
CPC ........... *H04R 25/70* (2013.01); *H04R 25/505* (2013.01); *H04R 25/554* (2013.01); *H04R 2225/43* (2013.01)

(58) Field of Classification Search
None
See application file for complete search history.

(56) References Cited

U.S. PATENT DOCUMENTS

| | | | |
|---|---|---|---|
| 5,987,147 A | 11/1999 | Nishimoto | |
| 7,113,589 B2 | 9/2006 | Mitchler | |
| 8,565,460 B2 | 10/2013 | Takagi et al. | |
| 8,761,421 B2 * | 6/2014 | Apfel ..................... | H04R 25/70 381/315 |

(Continued)

FOREIGN PATENT DOCUMENTS

| | | |
|---|---|---|
| KR | 20170026786 | 3/2017 |
| WO | 2019136382 | 7/2019 |

OTHER PUBLICATIONS

International Preliminary Report on Patentability—PCT/US2019/012550.
International Search Report—PCT/US2019/012550.

*Primary Examiner* — Tuan D Nguyen

(74) *Attorney, Agent, or Firm* — Scott Griggs; Griggs Bergen LLP

(57) ABSTRACT

A system and method for aiding hearing are disclosed. In one embodiment of the system, a programming interface is configured to communicate with a device. The system screens, via a speaker and a user interface associated with the device, a left ear—and separately, a right ear—of a patient at an incrementally selected frequency between a frequency range of 50 Hz to 5,000 Hz, with detected frequencies being re-ranged tested to better identify the frequencies and decibel levels heard. A frequency range of 5,000 Hz to 10,000 Hz is then tested. The system then determines a left ear preferred hearing range and a right ear preferred hearing range.

20 Claims, 9 Drawing Sheets

(56) References Cited

U.S. PATENT DOCUMENTS

| | | |
|---|---|---|
| 9,232,322 B2 | 1/2016 | Fang |
| 9,344,814 B2 | 5/2016 | Rasmussen |
| 9,712,928 B2 | 7/2017 | Pedersen et al. |
| 10,181,328 B2 | 1/2019 | Jensen et al. |
| 2004/0073138 A1* | 4/2004 | Greco .................. A61M 25/10 600/561 |
| 2013/0223661 A1* | 8/2013 | Uzuanis ............... H04R 25/505 381/314 |
| 2014/0314261 A1* | 10/2014 | Selig ..................... H04R 25/70 381/314 |
| 2015/0023512 A1* | 1/2015 | Shennib ................ H04R 25/70 381/60 |
| 2015/0023535 A1* | 1/2015 | Shennib ................ A61B 5/123 381/314 |
| 2016/0350821 A1* | 12/2016 | Shennib ............. G06Q 30/0601 |

* cited by examiner

US 10,893,370 B1

SYSTEM AND METHOD FOR AIDING HEARING

PRIORITY STATEMENT & CROSS-REFERENCE TO RELATED APPLICATIONS

This application is a continuation-in-part of co-pending U.S. patent application Ser. No. 17/026,955, entitled "Hearing Aid and Method for Use of Same" and filed on Sep. 21, 2020, in the names of Laslo Olah et al.; which claims the benefit of priority from (1) U.S. Provisional Patent Application No. 62/935,961, entitled "Hearing Aid and Method for Use of Same" and filed on Nov. 15, 2019 in the name of Laslo Olah; and (2) U.S. Provisional Patent Application No. 62/904,616, entitled "Hearing Aid and Method for Use of Same" and filed on Sep. 23, 2019, in the name of Laslo Olah; all of which are hereby incorporated by reference, in entirety, for all purposes. U.S. patent application Ser. No. 17/026,955, entitled "Hearing Aid and Method for Use of Same" and filed on Sep. 21, 2020, in the names of Laslo Olah et al. is also a continuation-in-part of co-pending U.S. patent application Ser. No. 16/959,972, entitled "Hearing Aid and Method for Use of Same" and filed on Jul. 2, 2020 in the name of Laslo Olah; which claims priority from International Application No. PCT/US19/12550, entitled "Hearing Aid and Method for Use of Same" and filed on Jan. 7, 2019 in the name of Laslo Olah; which claims priority from U.S. Provisional Patent Application No. 62/613,804, entitled "Hearing Aid and Method for Use of Same" and filed on Jan. 5, 2018 in the name of Laslo Olah; all of which are hereby incorporated by reference, in entirety, for all purposes.

TECHNICAL FIELD OF THE INVENTION

This invention relates, in general, to hearing aids and, in particular, to systems and methods that aid hearing to provide signal processing and feature sets to enhance speech and sound intelligibility.

BACKGROUND OF THE INVENTION

Hearing loss can affect anyone at any age, although elderly adults more frequently experience hearing loss. Untreated hearing loss is associated with lower quality of life and can have far-reaching implications for the individual experiencing hearing loss as well as those close to the individual. As a result, there is a continuing need for improved hearing aids and methods for use of the same that enable patients to better hear conversations and the like.

SUMMARY OF THE INVENTION

It would be advantageous to achieve a hearing aid and method for use of the same that would significantly change the course of existing hearing aids by adding features to correct existing limitations in functionality. It would also be desirable to enable a mechanical and electronics-based solution that would provide enhanced performance and improved usability with an enhanced feature set. To better address one or more of these concerns, a system and method for aiding hearing are disclosed. In one embodiment of the system, a programming interface is configured to communicate with a device. The system screens, via a speaker and a user interface associated with the device, a left ear—and separately, a right ear—of a patient at an incrementally selected frequency between a frequency range of 50 Hz to 5,000 Hz, with detected frequencies being re-ranged tested at a more discrete incrementally selected frequency to better identify the frequencies and decibel levels heard. A frequency range of 5,000 Hz to 10,000 Hz is then tested. The system then determines a left ear preferred hearing range and a right ear preferred hearing range. These and other aspects of the invention will be apparent from and elucidated with reference to the embodiments described hereinafter.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which.

DETAILED DESCRIPTION OF THE INVENTION

While the making and using of various embodiments of the present invention are discussed in detail below, it should be appreciated that the present invention provides many applicable inventive concepts, which can be embodied in a wide variety of specific contexts. The specific embodiments discussed herein are merely illustrative of specific ways to make and use the invention, and do not delimit the scope of the present invention.

Figure 1A:
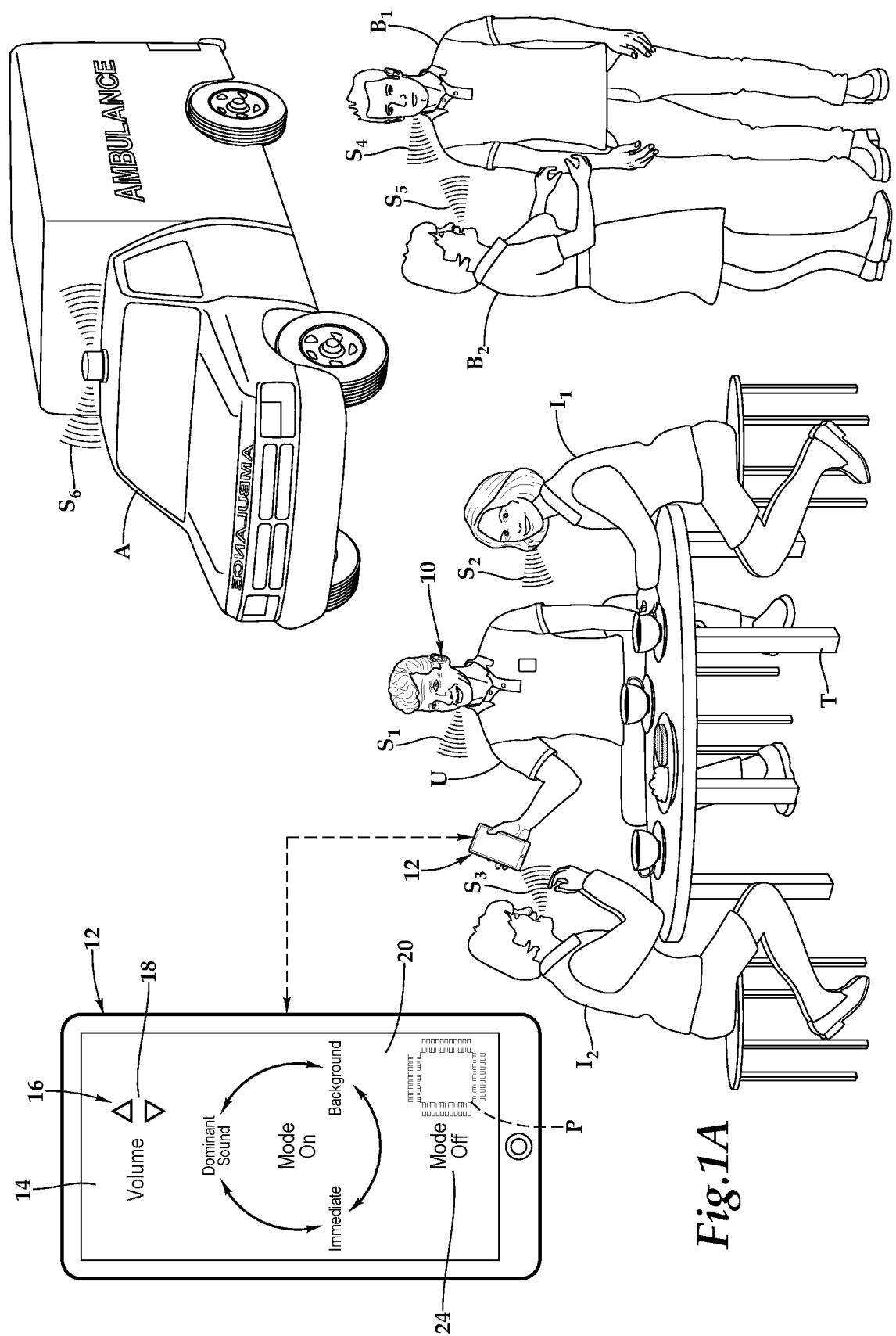
FIG. 1A is a front perspective schematic diagram depicting one embodiment of a hearing aid being programmed with a one embodiment of a system for aiding hearing, according to the teachings presented herein.
Figure 1B:
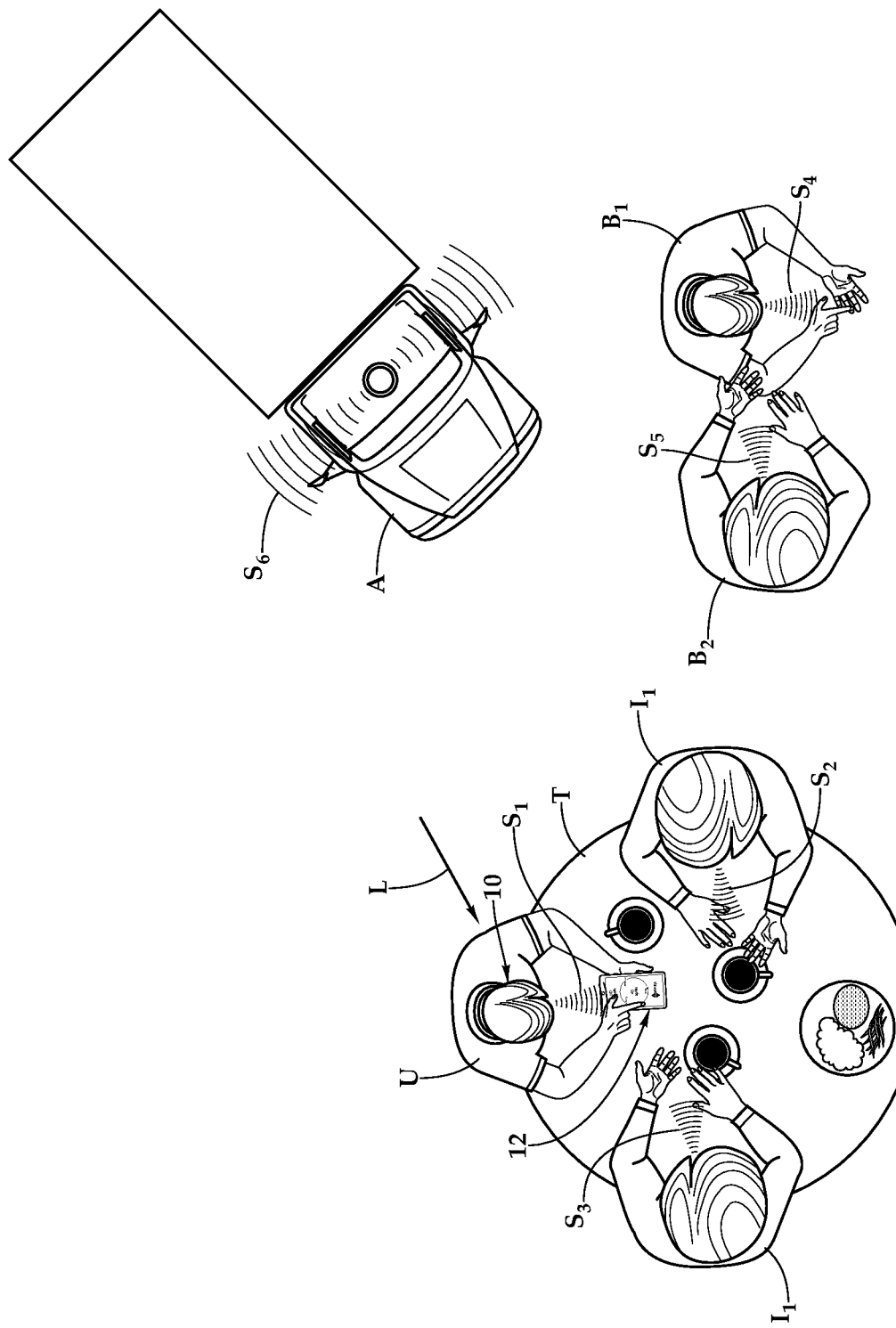
FIG. 1B is a top plan view depicting the hearing aid of FIG. 1A being utilized according to the teachings presented herein.

Referring initially to FIG. 1A and FIG. 1B, therein is depicted one embodiment of a hearing aid, which is schematically illustrated and designated 10. The hearing aid 10 is programmed according to a system for aiding hearing. As shown, a user U, who may be considered a patient requiring a hearing aid, is wearing the hearing aid 10 and sitting at a table T at a restaurant or café, for example, and engaged in a conversation with an individual $I_1$ and an individual $I_2$. As part of a conversation at the table T, the user U is speaking sound $S_1$, the individual $I_1$ is speaking sound $S_2$, and the individual 12 is speaking sound $S_3$. Nearby, in the background, a bystander $B_1$ is engaged in a conversation with a bystander $B_2$. The bystander $B_1$ is speaking sound $S_4$ and the bystander $B_2$ is speaking sound $S_5$. An ambulance A is driving by the table T and emitting sound $S_6$. The sounds $S_1$, $S_2$, and $S_3$ may be described as the immediate background sounds. The sounds $S_4$, $S_5$, and $S_6$ may be described as the background sounds. The sound $S_6$ may be described as the dominant sound as it is the loudest sound at table T.

As will be described in further detail hereinbelow, the hearing aid 10 is programmed with a qualified sound range for each ear in a two-ear embodiment and for one ear in a one-ear embodiment. As shown, in the two-ear embodiment, the qualified sound range may be a range of sound corresponding to a preferred hearing range for each ear of the user modified with a subjective assessment of sound quality according to the user. The preferred hearing range may be a range of sound corresponding to the highest hearing capacity of an ear of the user U between 50 Hz and 10,000 Hz. Further, as shown, in the two-ear embodiment, the preferred hearing range for each ear may be multiple ranges of sound corresponding to the highest hearing capacity ranges of an ear of the user U between 50 Hz and 10,000 Hz. In some embodiments of this multiple range of sound implementation, the various sounds $S_1$ through $S_6$ received may be transformed and divided into the multiple ranges of sound. In particular, the preferred hearing range for each ear may be an about 300 Hz frequency to an about 500 Hz frequency range of sound corresponding to highest hearing capacity of a patient.

The subjective assessment according to the user may include a completed assessment of a degree of annoyance caused to the user by an impairment of wanted sound. The subjective assessment according to the user may also include a completed assessment of a degree of pleasantness caused to the patient by an enablement of wanted sound. That is, the subjective assessment according to the user may include a completed assessment to determine best sound quality to the user. Sound received at the hearing aid 10 is converted to the qualified sound range prior to output, which the user U hears.

In one embodiment, the hearing aid 10 may create a pairing with a proximate smart device 12, such as a smart phone (depicted), smart watch, or tablet computer. The proximate smart device 12 includes a display 14 having an interface 16 having controls, such as an ON/OFF switch or volume controls 18 and mode of operation controls 20. A user may send a control signal wirelessly from the proximate smart device 12 to the hearing aid 10 to control a function, like volume controls 18. Further, in one embodiment, as shown by processor symbol P, after the hearing aid 10 creates the pairing with a proximate smart device 12, the hearing aid 10 and the proximate smart device 12 may leverage the wireless communication link therebetween and use processing distributed between the hearing aid 10 and the proximate smart device 12 to process the signals and perform other analysis.

Figure 2:
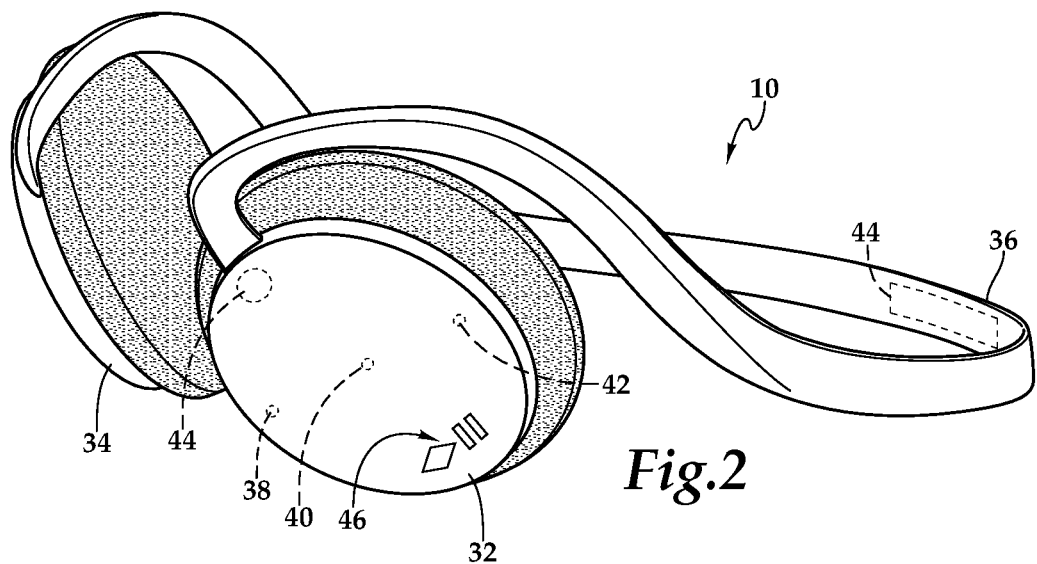
FIG. 2 is a front perspective view of one embodiment of the hearing aid depicted in FIG. 1.

Referring to FIG. 2, as shown, in the illustrated embodiment, the hearing aid 10 is programmed according to the system for aiding hearing and the hearing aid 10 includes a left body 32 and a right body 34 connected to a band member 36 that is configured to partially circumscribe the user U. Each of the left body 32 and the right body 34 cover an external ear of the user U and are sized to engage therewith. In some embodiments, microphones 38, 40, 42, which gather sound directionally and convert the gathered sound into an electrical signal, are located on the left body 32. With respect to gathering sound, the microphone 38 may be positioned to gather forward sound, the microphone 40 may be positioned to gather lateral sound, and the microphone 42 may be positioned to gather rear sound. Microphones may be similarly positioned on the right body 34. Various internal compartments 44 provide space for housing electronics, which will be discussed in further detail hereinbelow. Various controls 46 provide a patient interface with the hearing aid 10.

Having each of the left body 32 and the right body 34 cover an external ear of the user U and being sized to engage therewith confers certain benefits. Sound waves enter through the outer ear and reach the middle ear to vibrate the eardrum. The eardrum then vibrates the osciles, which are small bones in the middle ear. The sound vibrations travel through the osciles to the inner ear. When the sound vibrations reach the cochlea, they push against specialized cells known as hair cells. The hair cells turn the vibrations into electrical nerve impulses. The auditory nerve connects the cochlea to the auditory centers of the brain. When these electrical nerve impulses reach the brain, they are experienced as sound. The outer ear serves a variety of functions. The various air-filled cavities composing the outer ear, the two most prominent being the concha and the ear canal, have a natural or resonant frequency to which they respond best. This is true of all air-filled cavities. The resonance of each of these cavities is such that each structure increases the sound pressure at its resonant frequency by approximately 10 to 12 dB. In summary, among the functions of the outer ear: a) boost or amplify high-frequency sounds; b) provide the primary cue for the determination of the elevation of a sound's source; c) assist in distinguishing sounds that arise from in front of the listener from those that arise from behind the listener. Headsets are used in hearing testing in medical and associated facilities for a reason: tests have shown that completely closing the ear canal in order to prevent any form of outside noise plays direct role in acoustic matching. The more severe hearing problem, the closer the hearing aid speaker must be to the ear drum. However, the closer to the speaker is to the ear drum, the more the device plugs the canal and negatively impacts the ear's pressure system. That is, the various chambers of the ear have a defined operational pressure determined, in part, by the ear's structure. By plugging the ear canal, the pressure system in the ear is distorted and the operational pressure of the ear is negatively impacted.

As alluded, "plug size" hearing aids having limitations with respect to distorting the defined operational pressure within the ear. Considering the function of the outer ear's air filled cavities in increasing the sound pressure at resonant frequencies, the hearing aid of FIG. 2—and other figures— creates a closed chamber around the ear increasing the pressure within the chamber. This higher pressure plus the utilization of a more powerful speaker within the headset at qualified sound range, e.g., the frequency range the user hears best with the best quality sound, provide the ideal set of parameters for a powerful hearing aid.

Figure 3A:
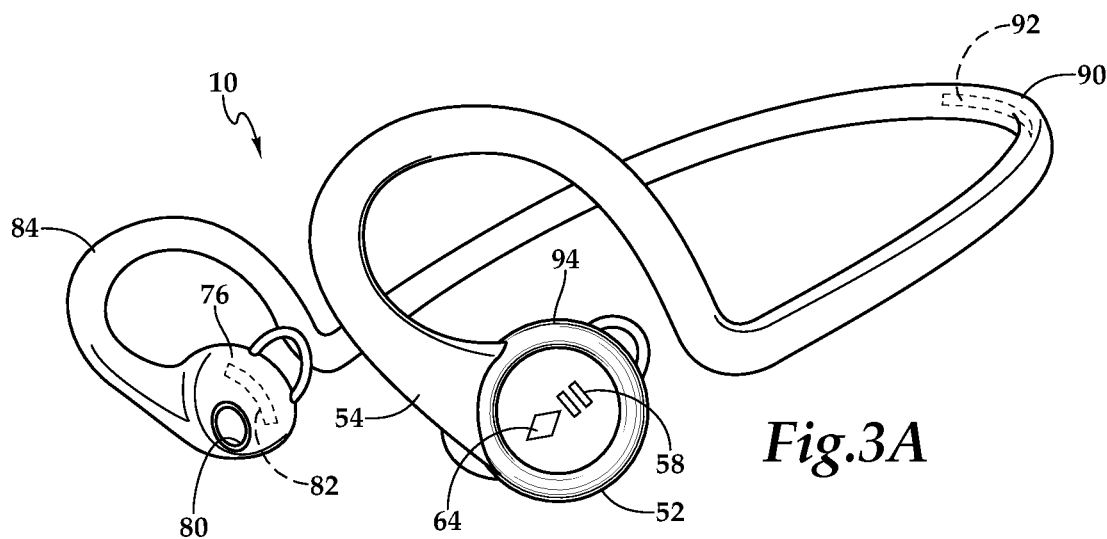
FIG. 3A is a front-left perspective view of another embodiment of the hearing aid depicted in FIG. 1.
Figure 3B:
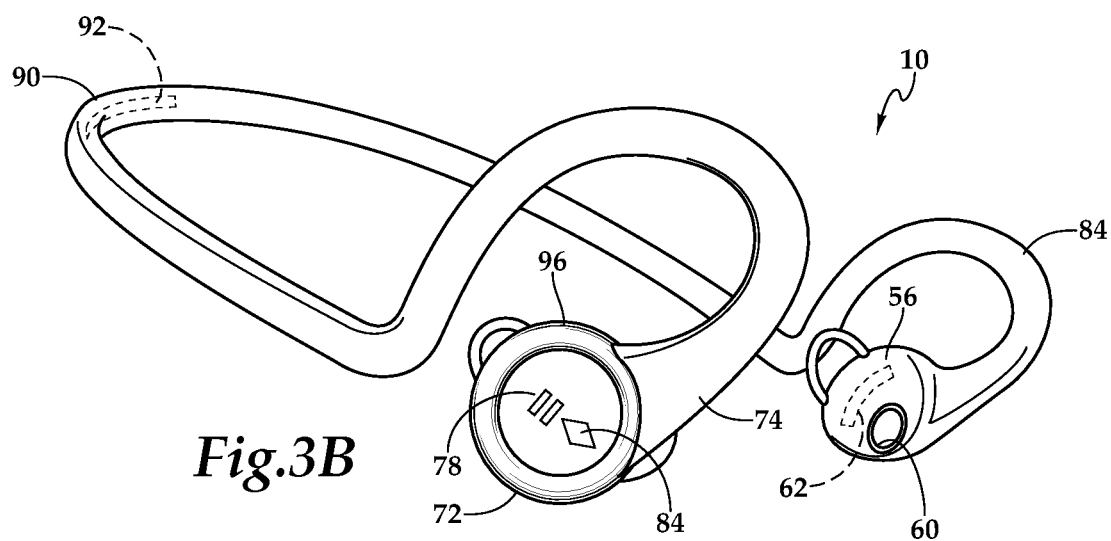
FIG. 3B is a front-right perspective view of the embodiment of the hearing aid depicted in FIG. 3A.

Referring to FIG. 3A and FIG. 3B, as shown, in the illustrated embodiment, the hearing aid 10 is programmed according to a system for aiding hearing and the hearing aid 10 includes a left body 52 having an ear hook 54 extending from the left body 52 to an ear mold 56. The left body 52 and the ear mold 56 may each at least partially conform to the contours of the external ear and sized to engage therewith. By way of example, the left body 52 may be sized to engage with the contours of the ear in a behind-the-ear-fit. The ear mold 56 may be sized to be fitted for the physical shape of a patient's ear. The ear hook 54 may include a flexible tubular material that propagates sound from the left body 52 to the ear mold 56. Microphones 58, which gather sound and convert the gathered sound into an electrical signal, are located on the left body 52. An opening 60 within the ear mold 56 permits sound traveling through the ear hook 54 to exit into the patient's ear. An internal compartment 62 provides space for housing electronics, which will be discussed in further detail hereinbelow. Various controls 64 provide a patient interface with the hearing aid 10 on the left body 52 of the hearing aid 10.

As also shown, the hearing aid 10 includes a right body 72 having an ear hook 74 extending from the right body 72 to an ear mold 76. The right body 72 and the ear mold 76 may each at least partially conform to the contours of the external ear and sized to engage therewith. By way of example, the right body 72 may be sized to engage with the contours of the ear in a behind-the-ear-fit. The ear mold 76 may be sized to be fitted for the physical shape of a patient's ear. The ear hook 74 may include a flexible tubular material that propagates sound from the right body 72 to the ear mold 76. Microphones 78, which gather sound and convert the gathered sound into an electrical signal, are located on the right body 72. An opening 80 within the ear mold 76 permits sound traveling through the ear hook 74 to exit into the patient's ear. An internal compartment 82 provides space for housing electronics, which will be discussed in further detail hereinbelow. Various controls 84 provide a patient interface with the hearing aid 10 on the right body 72 of the hearing aid 10. It should be appreciated that the various controls 64, 84 and other components of the left and right bodies 52, 72 may be at least partially integrated and consolidated. Further, it should be appreciated that the hearing aid 10 may have one or more microphones on each of the left and right bodies 52, 72 to improve directional hearing in certain implementations and provide, in some implementations, 360-degree directional sound input.

In one embodiment, the left and right bodies 52, are connected at the respective ear hooks 54, 74 by a band member 90 which is configured to partially circumscribe a head or a neck of the patient. A compartment 92 within the band member 90 may provide space for electronics and the like. Additionally, the hearing aid 10 may include left and right earpiece covers 94, 96 respectively positioned exteriorly to the left and right bodies 52, 72. Each of the left and right earpiece covers 94, 96 isolate noise to block out interfering outside noises. To add further benefit, in one embodiment, the microphones 58 in the left body 52 and the microphones 78 in the right body 72 may cooperate to provide directional hearing.

Figure 4:
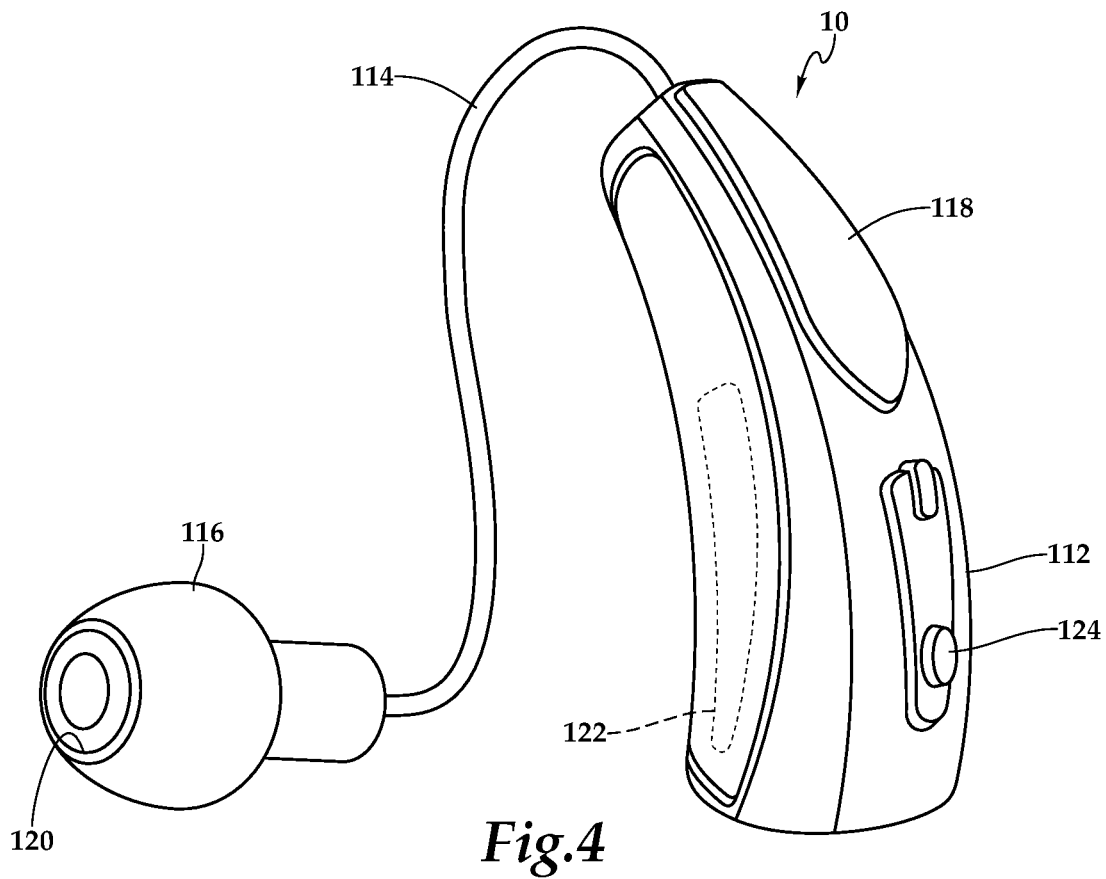
FIG. 4 is a front perspective view of another embodiment of programmed with one embodiment of a system for aiding hearing, according to the teachings presented herein.

Referring to FIG. 4, therein is depicted another embodiment of the hearing aid 10 that is programmed with the system for aiding hearing. It should be appreciated by a review of FIG. 2 through FIG. 4 that the system for aiding hearing presented herein may program any type of hearing aid. As shown, in the illustrated embodiment in FIG. 4, the hearing aid 10 includes a body 112 having an ear hook 114 extending from the body 112 to an ear mold 116. The body 112 and the ear mold 116 may each at least partially conform to the contours of the external ear and sized to engage therewith. By way of example, the body 112 may be sized to engage with the contours of the ear in a behind-the-ear-fit. The ear mold 116 may be sized to be fitted for the physical shape of a patient's ear. The ear hook 114 may include a flexible tubular material that propagates sound from the body 112 to the ear mold 116. A microphone 118, which gathers sound and converts the gathered sound into an electrical signal, is located on the body 112. An opening 120 within the ear mold 116 permits sound traveling through the ear hook 114 to exit into the patient's ear. An internal compartment 122 provides space for housing electronics, which will be discussed in further detail hereinbelow. Various controls 124 provide a patient interface with the hearing aid 10 on the body 112 of the hearing aid 10.

Figure 5:
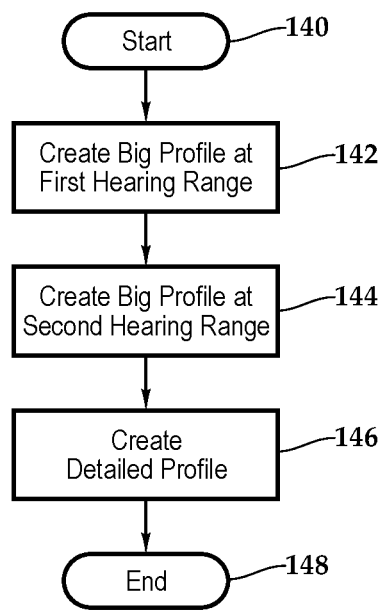
FIG. 5 is a flow chart depicting one method for aiding hearing, according to the teachings presented herein.

Referring now to FIG. 5, one embodiment of a method for aiding hearing is depicted. The methodology starts at block 140, when a patient is going to undergo screening to determine the preferred hearing range or preferred hearing ranges for programming a hearing aid, such as the hearing aid 10. At block 142, a big profile is created at a first hearing range. By way of example, an ear of a patient may be screened at an incrementally selected frequency between a frequency range of 50 Hz to 5,000 Hz, with detected frequencies noted. At block 144, another big profile is created, but at a second hearing range. By way of example, an ear of the patient may be screened at an incrementally selected frequency between a frequency range of 5,000 Hz to 10,000 Hz. At block 146, a detailed profile is created by re-ranged testing where hearing was noted to better identify the frequencies and decibel levels heard. This provides the preferred hearing range and the methodology ends at block 148.

Figure 6:
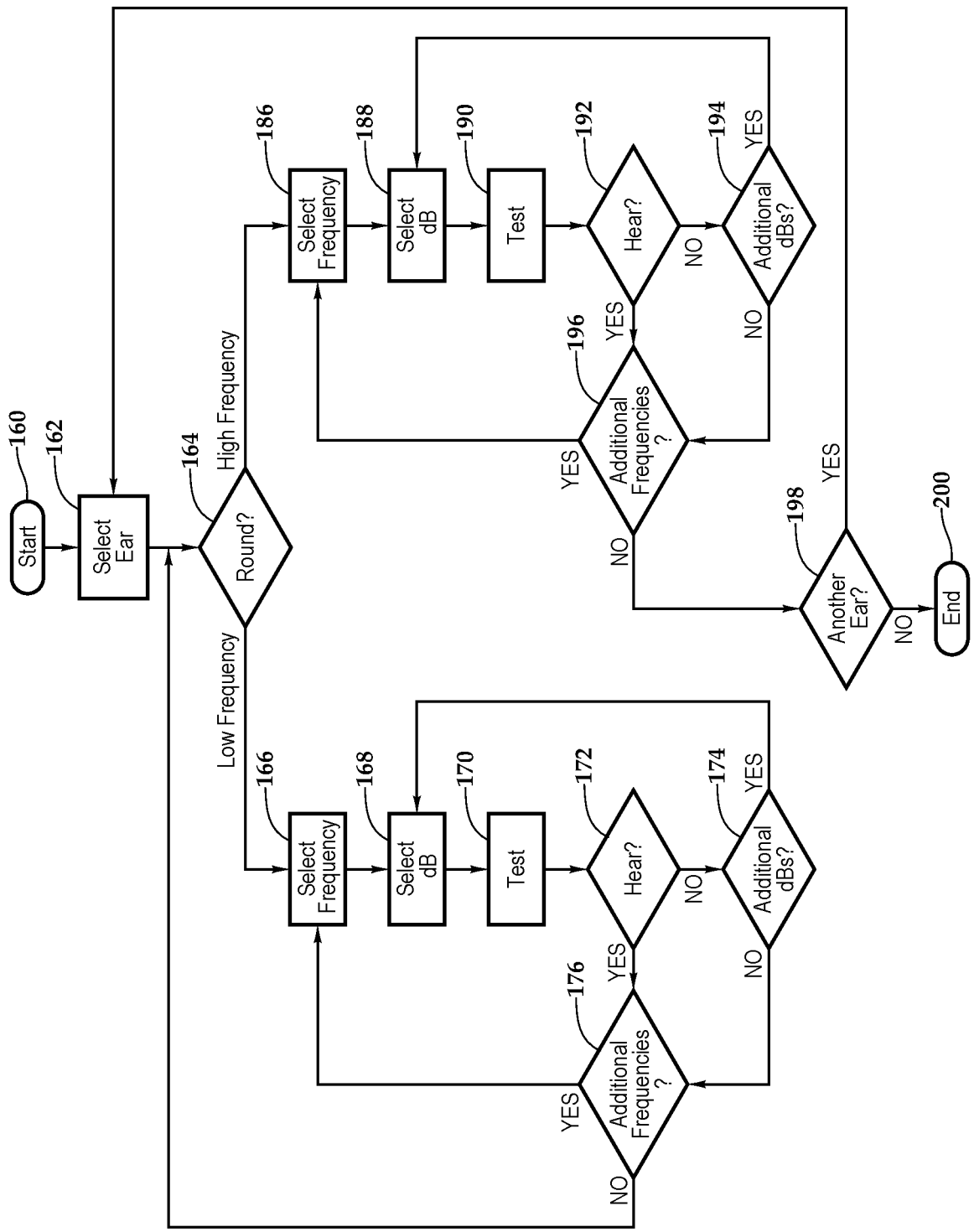
FIG. 6 is a flow chart depicting one embodiment of a method for calibrating and setting the hearing aid for a preferred hearing range or preferred hearing ranges, according to the teachings presented herein.

Referring now to FIG. 6, one embodiment of a method for calibrating and setting the hearing aid 10 for a preferred hearing range or preferred hearing ranges utilizing the methodology presented herein is shown. The method starts at block 160, when a patient is going to undergo testing to determine the preferred hearing range or preferred hearing ranges for use of the hearing aid 10. This method will provide the necessary calibration and settings for the hearing aid 10. The methodology screens a large number of hearing aid screening points and involve a methodology that is completely automated and overseen by an assistant. At block 162, an ear of the patient is selected. In one embodiment, a left ear preferred hearing range and a right ear preferred hearing range are determined corresponding to the left and right bodies 52, 72 of the hearing aid 10. Each of the left ear preferred hearing range and the right ear preferred hearing range may be a range of sounds corresponding to the highest hearing capacity of the respective ear of the patient. In one implementation, this range of sound is between 50 Hz and 10,000 Hz. Further, the left ear preferred hearing range and the right ear preferred hearing range may be mutually exclusive, at least partially overlap, or be identical. Further still, the left ear preferred hearing range or the right ear preferred hearing range may include multiple narrow hearing range bands. It should be appreciated that the profile of the left ear preferred hearing range and the right ear preferred hearing range will vary from patient to patient, i.e., user to user.

Once an ear is selected at block 162, the methodology proceeds to decision block 164, where a round of testing is selected. In one embodiment, the hearing aid testing requires two rounds of testing. In a low frequency round, the ear under test is tested between 50 Hz and 5,000 Hz, at a variable increment, such as a 50 Hz increment or other increment, initially with subsequent testing in a more discrete variable increment, such as a 5 Hz to 20 Hz increments, if hearing is detected. In a high frequency round, the ear under test is tested between 5,000 Hz and 10,000 Hz at a variable increment, such as a 200 Hz increment, initially with subsequent testing in a more discrete increment, such as a 5 Hz to 20 Hz increment, if hearing is detected to better identify the preferred hearing range, whether the left ear preferred hearing range or the right ear preferred hearing range. With low frequency testing selected, the methodology advances to block 166 where the frequency to be tested is selected. For the low frequency testing, the testing begins at 50 Hz and progressively is increased with a variable or constant increment to 5,000 Hz with subsequent iterations. At block 168, the decibel level is selected. The decibel level begins at 10 dB and increases to 120 dB with subsequent iterations. At block 170, the test sound at the selected frequency and decibel level is provided to the selected ear of the patient. At decision block 172, if the patient hears the test sound at the selected frequency and decibel level, then the patient pushes a button when the test sound is first heard. If the patient does not hear the test sound, then the methodology advances to decision block 174, where if there are additional decibels to test then the methodology returns to block 168, where, iteratively, the decibel level is increased and the testing continues at block 170, as previously discussed. On the other hand, if the decibel levels are exhausted and there are no more decibel levels to test, then the methodology advances to decision block 176. By way of example, at decision block 174, if the decibel level is at maximum strength, at 120 dBs, for example, then the decibel levels to test would be exhausted. It should be appreciated that in one implementation, the escalation of the decibel levels may be continuous during the testing or seem continuous to the patient during the testing.

Returning to decision block 172, if the test sound at the designated frequency and decibel level is heard, then the methodology advances to decision block 176. At decision block 176, if there are additional frequencies to test, then the methodology returns to block 166, where another frequency is selected. If all frequencies to be tested, then the methodology returns to block 164, where the high frequency round of testing is selected as the testing for the ear under test of the patient for the low frequency is completed. By way of example, if a test sound at a particular frequency and decibel was heard and the methodology advanced from decision block 172, then the frequencies around the test sound are tested at a 5 Hz to a 20 Hz increment in the methodology to identify the exact frequency range that is heard. By way of further example, if a test sound at a particular frequency and decibel were not heard and the methodology advanced from decision block 176, then the next frequency in the selected variable increment, such as a 50 Hz increment, from 50 Hz to 5,000 Hz will be selected at block 166. The methodology continues in this manner through block 166, block 168, block 170, decision block 172, decision block 174, and decision block 176 until, in the illustrated embodiment, all frequencies between 50 Hz and 5,000 Hz are tested at a variable increment, such as a 50 Hz increment, for example, at a decibel range of, for example, from 10 dB to 120 dB, with frequencies detected being ranged tested and retested at a 5 Hz to 20 Hz increment.

Once the low frequency testing is completed for an ear under test, then the methodology returns through block 162 where the ear under test is continued to be selected and at decision block 164 the high frequency testing is selected. In the high frequency testing, the methodology tests, in one embodiment, a frequency range of 5,000 Hz to 10,000 Hz at a variable increment, such as a 200 Hz increment or other increment, for example, at a decibel range of 10 dB to 120 dB, with detected frequencies to be re-range tested at a more discrete increment, such as a 5 Hz to 20 Hz increment, for example, to better identify the frequencies and decibel levels heard. This methodology is executed by block 186, block 188, block 190, decision block 192, decision block 194, and decision block 196, which execute a methodology similar to the block 166, the block 168, the block 170, the decision block 172, the decision block 174, and the decision block 176 discussed hereinabove. Once the high frequency testing is complete for the ear under test at decision block 196 and there are no more frequencies to be tested, then the methodology advances to decision block 198, where if there is another ear to be tested the methodology returns to block 162 for testing the new ear under test for both the low frequency and high frequency testing. On the other hand, if all ears to be tested have been tested then the methodology advances to block 200 where the testing methodology concludes. At block 200, with the testing complete, if both ears were tested, for example, then a left ear preferred hearing range and a right ear preferred hearing range will be documented that indicate the range or ranges of frequencies for each ear at particular decibel levels where the patient can hear. The left ear preferred hearing range and the right ear preferred hearing range are utilized to calibrate the hearing aid 10.

Figure 7:
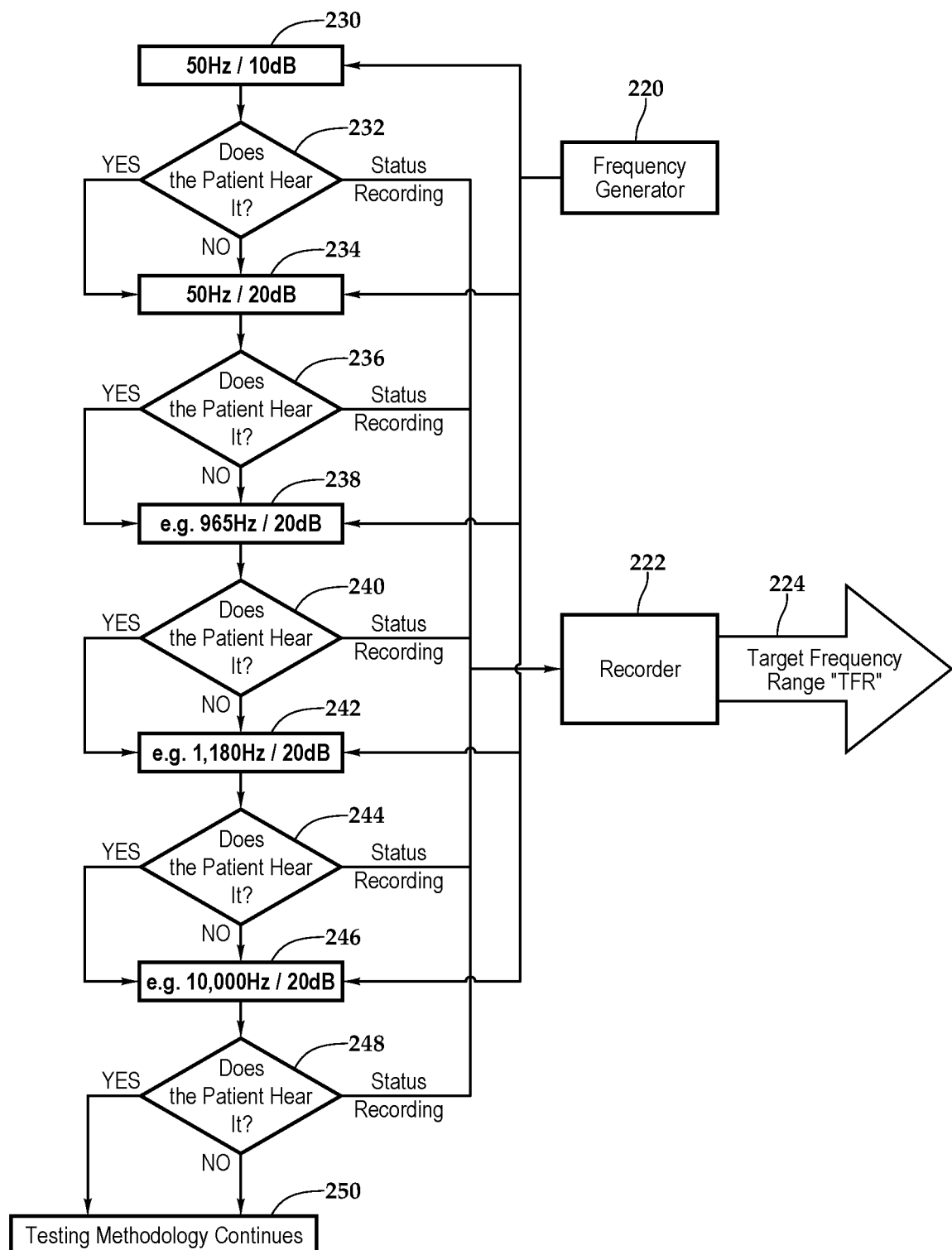
FIG. 7 is a flow chart depicting another embodiment of a method for calibrating and setting the hearing aid for a preferred hearing range or preferred hearing ranges, according to the teachings presented herein.

Referring now to FIG. 7, another embodiment of a method for calibrating and setting the hearing aid 10 for a preferred hearing range or preferred hearing ranges utilizing the methodology presented herein is shown. A frequency generator 220 and recorder 222 interact with the methodology to provide a target frequency range 224 and one or more of the target frequency ranges 224 may be combined to arrive at the preferred hearing range. As will be discussed in further detail hereinbelow, the frequency generator 220 and the recorder 222 may be embodied on any combination of smart devices, servers, and hearing aid test equipment.

At block 230, an initial frequency of 50 Hz at 10 dB is screened. As shown by decision block 232, the patient's ability to hear the initial frequency is recorded before the process advances to the next frequency of 50 Hz (or other variable increment) at 20 dB at block 234 and the patient's ability to hear is recorded at decision block 236. At block 238 and decision block 240, the process continues for the next incremental frequency, e.g., 965 Hz at 20 dB. Similarly, at block 242 and decision block 244, the methodology advances for 1,180 Hz at 20 Db before the process advances to block 246 and decision block 248 for 10,000 Hz at 20 dB. As indicated in block 250, the testing methodology continues for the frequencies under test with the results being recorded.

Figure 8:
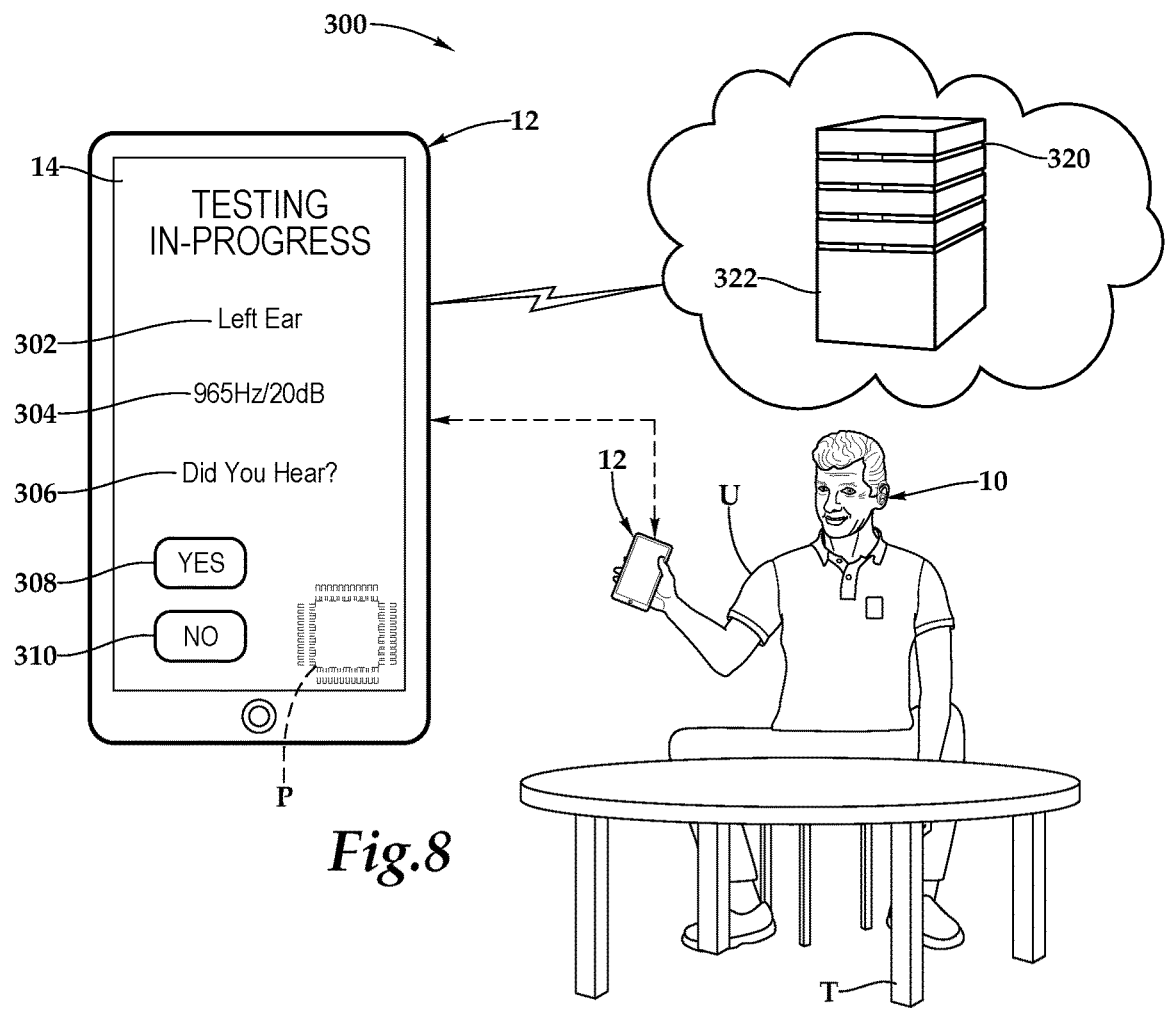
FIG. 8 is a perspective schematic diagram depicting one embodiment of a system for aiding hearing, according to the teachings presented herein.

Referring now to FIG. 8, one embodiment of a system 300 for aiding hearing is shown. As shown, the user U, who may be considered a patient requiring a hearing aid, is wearing the hearing aid 10 and sitting at a table T. The hearing aid 10 has a pairing with the proximate smart device 12 such the hearing aid 10 and the proximate smart device 12 may determine the user's preferred hearing range for each ear and subsequently program the hearing aid 10 with the preferred hearing ranges. The proximate smart device 12, which may be a smart phone, a smart watch, or a tablet computer, for example, is executing a hearing screening program. The display 14 serves as an interface for the user U. As shown, various indicators, such as indicators 302, 304, 306 show that the testing of the left ear is in progress at 965 Hz at 20 db. The user U is asked if the sound was heard at the indicator 306 and the user U may appropriately respond at soft button 308 or soft button 310. In this way, the system 300 screens, via a speaker and a user interface associated with the proximate smart device 12, a left ear—and separately, a right ear—of the user U at an incrementally selected frequency between a frequency range of 50 Hz to 5,000 Hz, with detected frequencies being re-ranged tested with a more discrete increment to better identify the frequencies and decibel levels heard. A frequency range of 5,000 Hz to 10,000 Hz is then tested. The system then determines a left ear preferred hearing range and a right ear preferred hearing range.

As shown the proximate smart device 12 may be in communication with a server 320 having a housing 322. The smart device may utilize distributed processing between the proximate smart device 12 and the server 320 to at least one of screen the left ear, screen the right ear, determine the left ear preferred hearing range, and determine the right ear preferred hearing range. As previously mentioned, the processing to screen the left ear, screen the right ear, determine the left ear preferred hearing range, and determine the right ear preferred hearing range may be located on a smart device, a server, hearing testing equipment, or any combination thereof.

Figure 9:
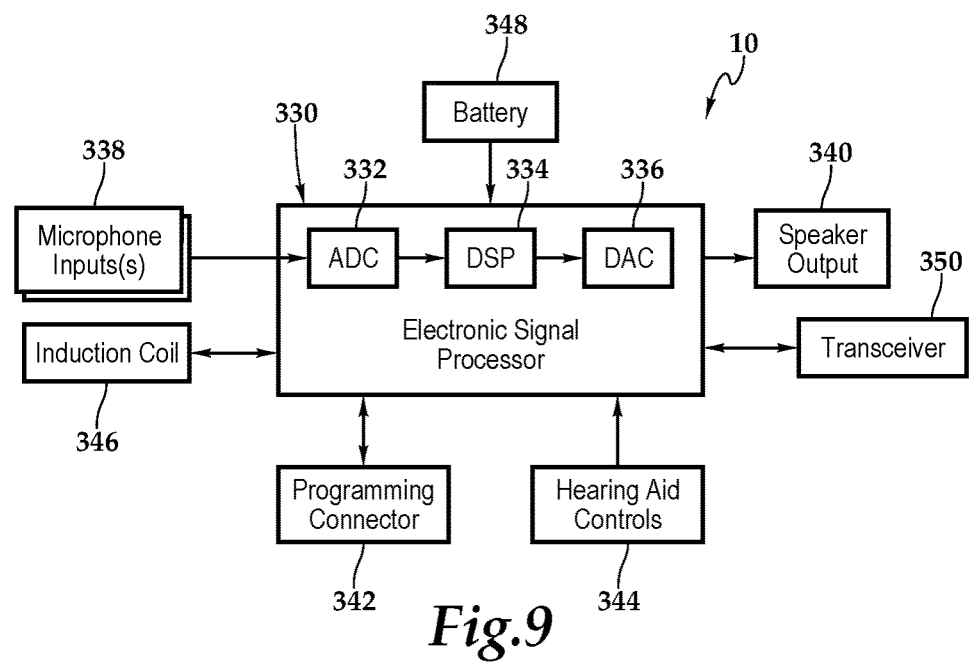
FIG. 9 is a functional block diagram depicting one embodiment of the hearing aid depicted in FIG. 8.

Referring now to FIG. 9, an illustrative embodiment of the internal components of the hearing aid 10 is depicted. By way of illustration and not by way of limitation, the hearing aid 10 depicted in the embodiment of FIG. 2 and FIGS. 3A, 3B is presented. It should be appreciated, however, that the teachings of FIG. 5 equally apply to the embodiment of FIG. 4. As shown, with respect to FIGS. 3A and 3B, in one embodiment, within the internal compartments 62, 82, an electronic signal processor 330 may be housed. The hearing aid 10 may include an electronic signal processor 330 for each ear or the electronic signal processor 330 for each ear may be at least partially integrated or fully integrated. In another embodiment, with respect to FIG. 4, within the internal compartment 122 of the body 112, the electronic signal processor 330 is housed. In order to measure, filter, compress, and generate, for example, continuous real-world analog signals in form of sounds, the electronic signal processor 330 may include an analog-to-digital converter (ADC) 332, a digital signal processor (DSP) 334, and a digital-to-analog converter (DAC) 336. The electronic signal processor 330, including the digital signal processor embodiment, may have memory accessible to a processor. One or more microphone inputs 338 corresponding to one or more respective microphones, a speaker output 340, various controls, such as a programming connector 342 and hearing aid controls 344, an induction coil 346, a battery 348, and a transceiver 350 are also housed within the hearing aid 10.

As shown, a signaling architecture communicatively interconnects the microphone inputs 338 to the electronic signal processor 330 and the electronic signal processor 330 to the speaker output 340. The various hearing aid controls 344, the induction coil 346, the battery 348, and the transceiver 350 are also communicatively interconnected to the electronic signal processor 330 by the signaling architecture. The speaker output 340 sends the sound output to a speaker or speakers to project sound and in particular, acoustic signals in the audio frequency band as processed by the hearing aid 10. By way of example, the programming connector 342 may provide an interface to a computer or other device and, in particular, the programming connector 342 may be utilized to program and calibrate the hearing aid 10 with the system 300, according to the teachings presented herein. The hearing aid controls 344 may include an ON/OFF switch as well as volume controls, for example. The induction coil 346 may receive magnetic field signals in the audio frequency band from a telephone receiver or a transmitting induction loop, for example, to provide a telecoil functionality. The induction coil 346 may also be utilized to receive remote control signals encoded on a transmitted or radiated electromagnetic carrier, with a frequency above the audio band. Various programming signals from a transmitter may also be received via the induction coil 346 or via the transceiver 350, as will be discussed. The battery 348 provides power to the hearing aid 10 and may be rechargeable or accessed through a battery compartment door (not shown), for example. The transceiver 350 may be internal, external, or a combination thereof to the housing. Further, the transceiver 350 may be a transmitter/receiver, receiver, or an antenna, for example. Communication between various smart devices and the hearing aid 10 may be enabled by a variety of wireless methodologies employed by the transceiver 150, including 802.11, 3G, 4G, Edge, WiFi, ZigBee, near field communications (NFC), Bluetooth low energy, and Bluetooth, for example.

The various controls and inputs and outputs presented above are exemplary and it should be appreciated that other types of controls may be incorporated in the hearing aid 10. Moreover, the electronics and form of the hearing aid 10 may vary. The hearing aid 10 and associated electronics may include any type of headphone configuration, a behind-the-ear configuration, an in-the-ear configuration, or in-the-ear configuration, for example. Further, as alluded, electronic configurations with multiple microphones for directional hearing are within the teachings presented herein. In some embodiments, the hearing aid has an over-the-ear configuration where the entire ear is covered, which not only provides the hearing aid functionality but hearing protection functionality as well.

Continuing to refer to FIG. 9, in one embodiment, the electronic signal processor 330 may be programmed with a preferred hearing range which, in one embodiment, is the preferred hearing sound range corresponding to highest hearing capacity of a patient. In one embodiment, the left ear preferred hearing range and the right ear preferred hearing range are each a range of sound corresponding to highest hearing capacity of an ear of a patient between 50 Hz and 10,000 Hz. The preferred hearing sound range for each of the left ear and the right ear may be an about 300 Hz frequency to an about 500 Hz frequency range of sound. With this approach, the hearing capacity of the patient is enhanced. Existing audiogram hearing aid industry testing equipment measures hearing capacity at defined frequencies, such as 60 Hz; 125 Hz; 250 Hz; 500 Hz; 1,000 Hz; 2,000 Hz; 4,000 Hz; 8,000 Hz and existing hearing aids work on a ratio-based frequency scheme. The present teachings however measure hearing capacity at a small step, such as 5 Hz, 10 Hz, or 20 Hz. Thereafter, one or a few, such as three, frequency ranges are defined to serve as the preferred hearing range or preferred hearing ranges. As discussed herein, in some embodiments of the present approach, a two-step process is utilized. First, hearing is tested in an ear between 50 Hz and 5,000 Hz at a variable increment, such as a 50 Hz increment or other increment, for example, and between 5,000 Hz and 10,0000 Hz at a variable increment, such as a 200 Hz increment, for example, to identify potential hearing ranges. Then, in the second step, the testing may be switched to a more discrete increment, such as a 5 Hz, 10 Hz, or 20 Hz increment, for example, to precisely identify the preferred hearing range.

Further, in one embodiment, with respect to FIG. 4, the various controls 344 may include an adjustment that widens the about frequency range of about 200 Hz, for example, to a frequency range of 100 Hz to 700 Hz or even wider, for example. Further, the preferred hearing sound range may be shifted by use of various controls 124. Directional microphone systems on each microphone position and processing may be included that provide a boost to sounds coming from the front of the patient and reduce sounds from other directions. Such a directional microphone system and processing may improve speech understanding in situations with excessive background noise. Digital noise reduction, impulse noise reduction, and wind noise reduction may also be incorporated. As alluded to, system compatibility features, such as FM compatibility and Bluetooth compatibility, may be included in the hearing aid 10.

Figure 10:
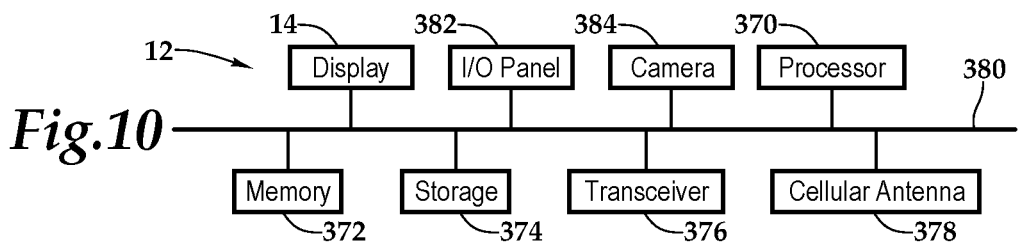
FIG. 10 is a functional block diagram of a smart device, which forms a portion of the system for aiding hearing depicted in FIG. 8.

Referring now to FIG. 10, the proximate smart device 12 may be a wireless communication device of the type including various fixed, mobile, and/or portable devices. To expand rather than limit the discussion of the proximate smart device 12, such devices may include, but are not limited to, cellular or mobile smart phones, tablet computers, smartwatches, and so forth. The proximate smart device 12 may include a processor 370, memory 372, storage 374, a transceiver 376, and a cellular antenna 378 interconnected by a busing architecture 380 that also supports the display 14, I/O panel 382, and a camera 384. It should be appreciated that although a particular architecture is explained, other designs and layouts are within the teachings presented herein.

The proximate smart device 12 includes the memory 372 accessible to the processor 370 and the memory 372 includes processor-executable instructions that, when executed, cause the processor 370 to screen, via the speaker and the user interface, a left ear of a patient at an incrementally selected frequency between a frequency range of 50 Hz to 5,000 Hz at a variable increment, such as a 50 Hz increment, for example, or other increment, at a decibel range of 10 db to 120 db, with detected frequencies being re-ranged tested at a 5 Hz to 20 Hz increment. Also the processor-executable instructions cause the processor 370 to screen, via the speaker and the user interface, the left ear of the patient at an incrementally selected frequency between a frequency range of 5,000 Hz to 10,000 Hz in a variable increment, such as a 200 Hz increment, for example, at a decibel range of 10 dB to 120 dB, with detected frequencies to be re-range tested at a more discrete increment, such as a 5 Hz to 20 Hz increment.

The processor-executable instructions may also determine a left ear preferred hearing range, which is a range of sound corresponding to highest hearing capacity of the left ear of the patient between 50 Hz and 10,000 Hz. The processor-executable instructions then cause the processor 370 to screen, via the speaker and the user interface, a right ear of the patient at an incrementally selected frequency between a frequency range of 50 Hz to 5,000 Hz at a variable increment, such as a 50 Hz increment, for example, or other increment, at a decibel range of 10 db to 120 db, with detected frequencies being re-ranged tested at a 5 Hz to 20 Hz increment. Similarly, the processor 370 is caused to screen, via the speaker and the user interface, the right ear of the patient at an incrementally selected frequency between a frequency range of 5,000 Hz to 10,000 Hz at a variable increment, such as a 200 Hz increment, for example, at a decibel range of 10 dB to 120 dB, with detected frequencies to be re-range tested at a more discrete variable increment, such as a 5 Hz to 20 Hz increment, for example. Then a left ear preferred hearing range is determined, which is a range of sound corresponding to highest hearing capacity of the left ear of the patient between 50 Hz and 10,000 Hz. Also, the processor executable instructions may cause the processor 370 to, when executed, utilize distributed processing between the proximate smart device 12 and a server to at least one of screen the left ear, screen the right ear, determine the left ear preferred hearing range, and determine the right ear preferred hearing range.

After the hearing aid 10 is programmed, in operation, the teachings presented herein permit the proximate smart device 12 such as a smart phone to form a pairing with the hearing aid 10 and operate the hearing aid 10. As shown, the proximate smart device 12 includes the memory 372 accessible to the processor 370 and the memory 372 includes processor-executable instructions that, when executed, cause the processor 370 to provide an interface for an operator that includes an interactive application for viewing the status of the hearing aid 10. The processor 370 is caused to present a menu for controlling the hearing aid 10. The processor 370 is then caused to receive an interactive instruction from the user and forward a control signal via the transceiver 376, for example, to implement the instruction at the hearing aid 10. The processor 370 may also be caused to generate various reports about the operation of the hearing aid 10. The processor 370 may also be caused to translate or access a translation service for the audio.

Figure 11:
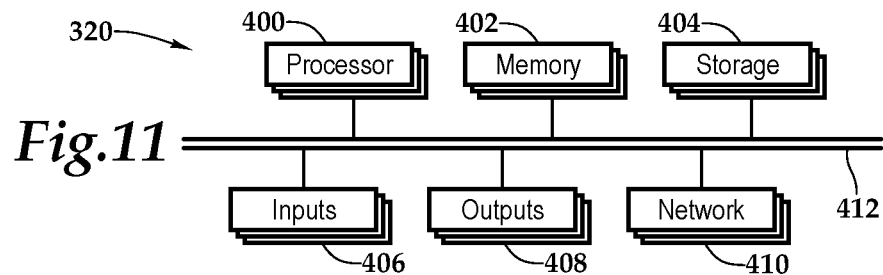
FIG. 11 is a functional block diagram depicting one embodiment of a server, which forms a portion of the system for aiding hearing depicted in FIG. 8.

Referring now to FIG. 11, one embodiment of the server 120 as a computing device includes, within the housing 322, a processor 400, memory 402, and storage 404 interconnected with various buses 412 in a common or distributed, for example, mounting architecture that also supports inputs 406, outputs 408, and network interface 410. In other implementations, in the computing device, multiple processors and/or multiple buses may be used, as appropriate, along with multiple memories and types of memory. Further still, in other implementations, multiple computing devices may be provided and operations distributed therebetween. The processor 400 may process instructions for execution within the server 320, including instructions stored in the memory 402 or in storage 404. The memory 402 stores information within the computing device. In one implementation, the memory 402 is a volatile memory unit or units. In another implementation, the memory 402 is a non-volatile memory unit or units. Storage 404 includes capacity that is capable of providing mass storage for the server 320, including crane service database storage capacity. Various inputs 406 and outputs 408 provide connections to and from the server 320, wherein the inputs 406 are the signals or data received by the server 320, and the outputs 408 are the signals or data sent from the server 320. The network interface 410 provides the necessary device controller to connect the server 320 to one or more networks.

The memory 402 is accessible to the processor 400 and includes processor-executable instructions that, when executed, cause the processor 400 to execute a series of operations. The processor 400 may be caused to screen, via the speaker and the user interface, a left ear of a patient at an incrementally selected frequency between a frequency range of 50 Hz to 5,000 Hz at a variable increment, such as a 50 Hz increment, for example, at a decibel range of 10 db to 120 db, with detected frequencies being re-ranged tested at a more discrete variable increment, such as a 5 Hz to 20 Hz increment. Also the processor-executable instructions cause the processor 400 to screen, via the speaker and the user interface, the left ear of the patient at an incrementally selected frequency between a frequency range of 5,000 Hz to 10,000 Hz at a variable increment, such as a 200 Hz increment, for example, at a decibel range of 10 dB to 120 dB, with detected frequencies to be re-range tested at a more discrete increment, such as a 5 Hz to 20 Hz increment.

The processor-executable instructions may also determine a left ear preferred hearing range, which is a range of sound corresponding to highest hearing capacity of the left ear of the patient between 50 Hz and 10,000 Hz. The processor-executable instructions then cause the processor 400 to screen, via the speaker and the user interface, a right ear of the patient at an incrementally selected frequency between a frequency range of 50 Hz to 5,000 Hz at a variable increment, such as a 50 Hz increment, for example, at a decibel range of 10 db to 120 db, with detected frequencies being re-ranged tested at a more discrete variable increment, such as a 5 Hz to 20 Hz increment, for example. Similarly, the processor 400 is caused to screen, via the speaker and the user interface, the right ear of the patient at an incrementally selected frequency between a frequency range of 5,000 Hz to 10,000 Hz at a variable increment, such as a 200 Hz increment, for example, at a decibel range of 10 dB to 120 dB, with detected frequencies to be re-range tested at a more discrete increment, such as a 5 Hz to 20 Hz increment. Then a left ear preferred hearing range is determined, which is a range of sound corresponding to highest hearing capacity of the left ear of the patient between 50 Hz and 10,000 Hz. Also, the processor executable instructions may cause the processor 400 to, when executed, utilize distributed processing between the server 320 and either the proximate smart device 12 or hearing testing equipment to at least one of screen the left ear, screen the right ear, determine the left ear preferred hearing range, and determine the right ear preferred hearing range.

Figure 12:
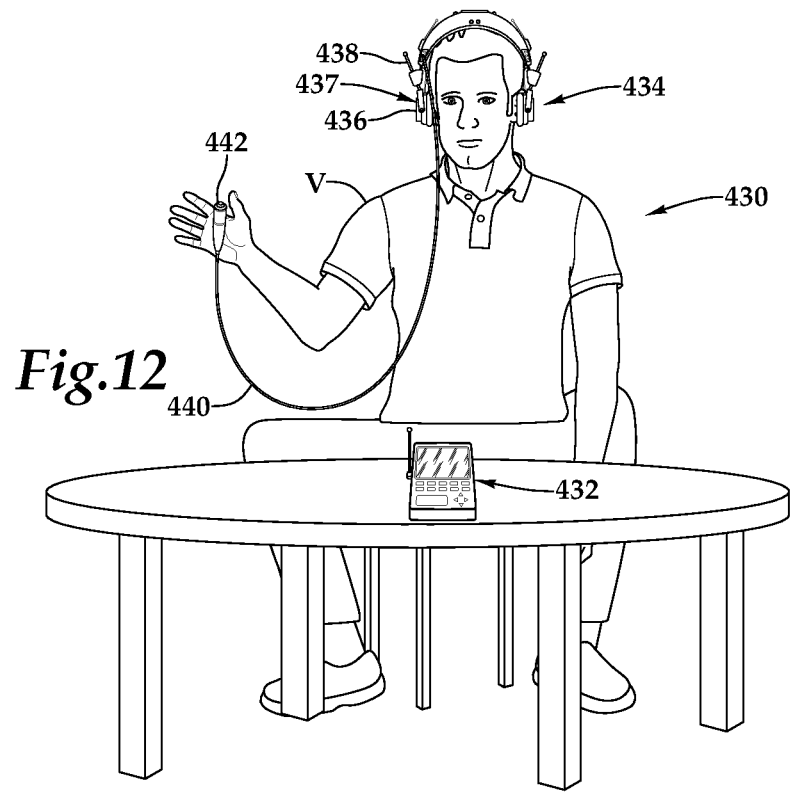
FIG. 12 is a perspective schematic diagram depicting another embodiment of a system for aiding hearing, according to the teachings presented herein.

Referring now FIG. 12, another embodiment of a system 430 for aiding hearing is shown. As shown, a user V, who may be considered a patient requiring a hearing aid, is utilizing hearing testing device 434 with a testing/programming unit 432 and a headset 436 having headphones 437 with a transceiver 438 for communicating with the hearing testing device 434. A push button 442 is coupled with cabling 440 to the headset 436 to provide an interface for the user V to indicate when a particular sound, i.e., frequency and decibel is heard. In this way, the system 430 screens, via a speaker in the headset 436 and a user interface with the push button 442, a left ear—and separately, a right ear—of the user V at an incrementally selected frequency between a frequency range of 50 Hz to 5,000 Hz, with detected frequencies being re-ranged tested to better identify the frequencies and decibel levels heard. A frequency range of 5,000 Hz to 10,000 Hz is then tested. The system then determines a left ear preferred hearing range and a right ear preferred hearing range.

Figure 13:
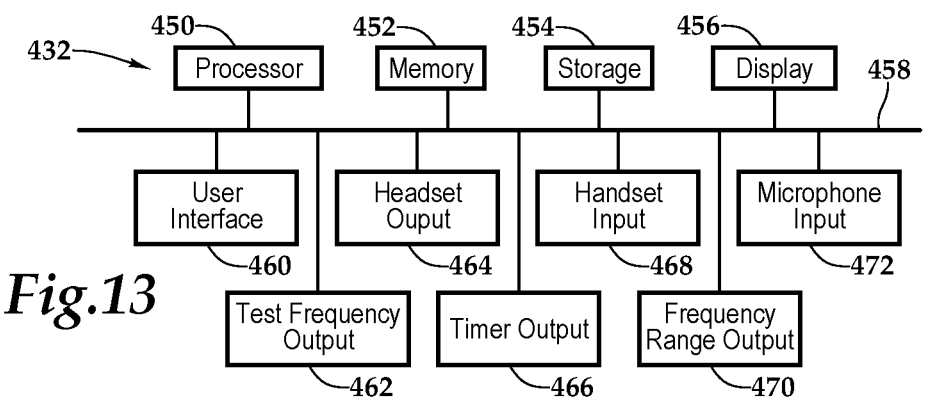
FIG. 13 is a functional block diagram depicting one embodiment of hearing aid test equipment depicted in FIG. 12.

Referring now to FIG. 13, the hearing testing device 434 depicted as a computing device is shown. Within a housing (not shown), a processor 450, memory 452, storage 454, and a display 456 are interconnected by a busing architecture 458 within a mounting architecture. The processor 450 may process instructions for execution within the computing device, including instructions stored in the memory 452 or in storage 454. The memory 452 stores information within the computing device. In one implementation, the memory 452 is a volatile memory unit or units. In another implementation, the memory 452 is a non-volatile memory unit or units. The storage 454 provides capacity that is capable of providing mass storage for the hearing testing device 434. Various inputs and outputs provide connections to and from the computing device, wherein the inputs are the signals or data received by the hearing testing device 434, and the outputs are the signals or data sent from the hearing testing device 434. In the following description, it should be appreciated that various inputs and outputs may be partially or fully integrated.

By way of example, with respect to inputs and outputs, the hearing testing device 432 may include the display 456, a user interface 460, a test frequency output 462, a headset output 464, a timer output 466, a handset input 468, a frequency range output 470, and a microphone input 472. The display 456 is an output device for visual information, including real-time or post-test screening results. The user interface 460 may provide a keyboard or push button for the operator of the hearing testing device 432 to provide input, including such functions as starting the screening, stopping the screening, and repeating a previously completed step. The test frequency output 462 may display the range to be examined, such as a frequency between 100 Hz and 5,000 Hz. The headset output 464 may output the signal under test to the patient. The timer output 466 may include an indication of the length of time the hearing testing device 432 will stay on a given frequency. For example, the hearing testing device 432 may stay 30 seconds on a particular frequency. The handset input 468 may be secured to a handset that provides "pause" and "okay" functionality for the patient during the testing. The frequency range output 462 may indicate the test frequency range per step, such as the aforementioned variable increment, which may be 50 Hz or another value, for example. The microphone input 472 receives audio input from the operator relative to screening instructions intended for the patient, for example.

The memory 452 and the storage 454 are accessible to the processor 450 and include processor-executable instructions that, when executed, cause the processor 450 to execute a series of operations. With respect to processor-executable instructions, the processor-executable instructions may cause the processor 450 to permit the hearing testing device 432 to be conducted by one ear at a time. The processor-executable instructions may also cause the processor 450 to permit the patient to pause the process in response to a signal received at the handset input 468. As part of the processor-executable instructions, the processor 450, between 50 Hz and 5,000 Hz, may be caused to start the hearing testing device 432 at 50 Hz by giving a 50 Hz signal—or other variably set increment—for a predetermined length of time, such as 20 seconds to 30 seconds starting at 10 db and stopping at 120 db. The processor-executable instructions may cause the processor 450 to receive a detection signal from the handset input 468 during screening. Then, the processor-executable instructions cause the hearing testing device 432 to test to the next frequency at a step, such as 100 Hz, for example, and continue the screening process.

As part of the processor-executable instructions, the processor 450, between 5,000 Hz and 10,000 Hz, may be caused to start the hearing test device 434 at 5,200 Hz by giving a 5,200 Hz signal for a predetermined length of time, such as 20 seconds to 30 seconds starting at 10 db and stopping at 120 db. The processor-executable instructions may cause the processor 450 to receive a detection signal from the handset input 468 during screening. Then, the processor-executable instructions cause the hearing test device 434 to test to the next frequency at as step, such as 5,400 Hz, for example, and continue the screening process. The processor-executable instructions may cause the screening for the designated ear to be complete at 5,400 Hz at which time the entire process may start over for another ear or another patient. The system then determines a left ear preferred hearing range and a right ear preferred hearing range.

Figure 14:
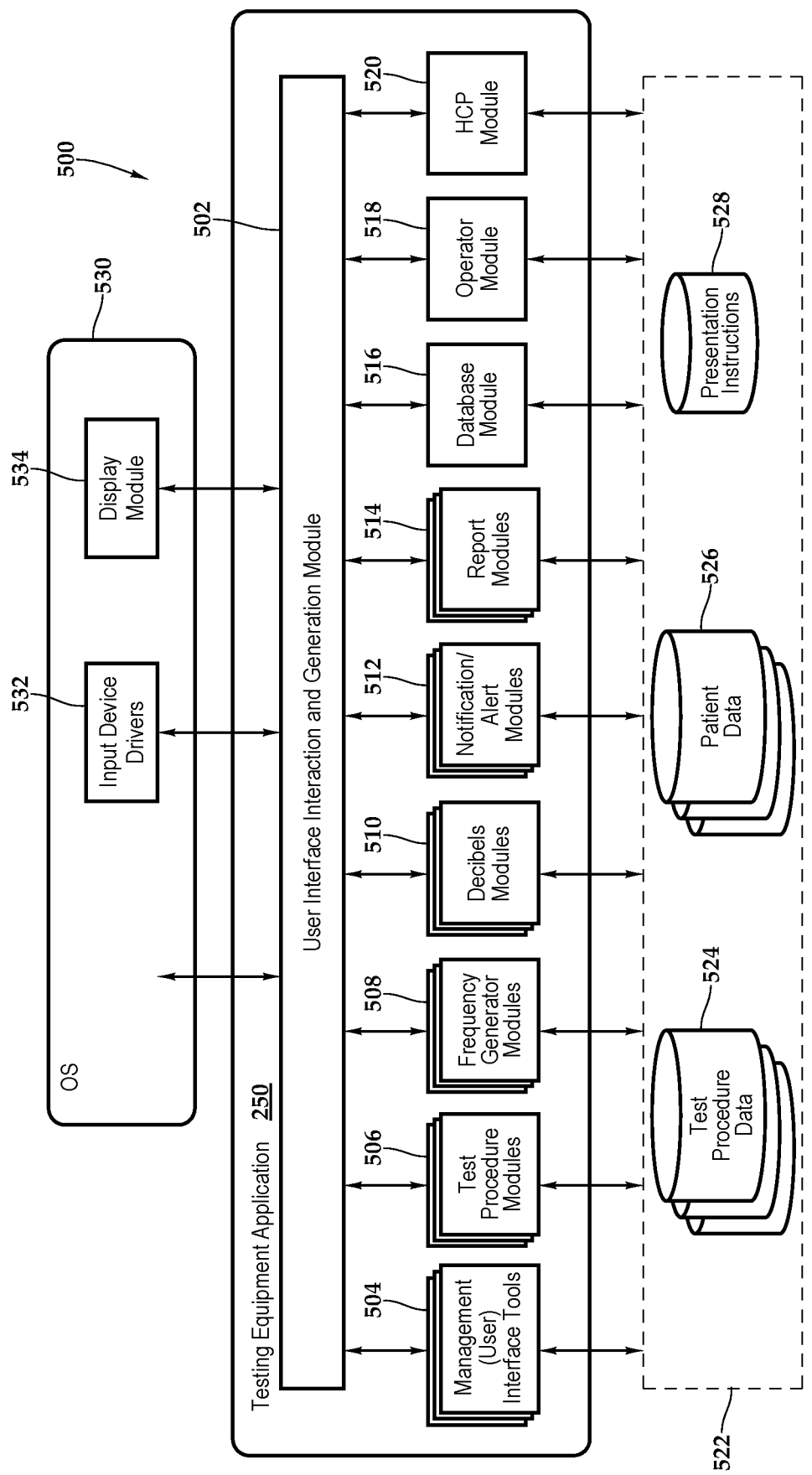
FIG. 14 is a conceptual module diagram depicting a software architecture of a testing equipment application of some embodiments.

Referring now to FIG. 14, conceptually illustrates the software architecture of a testing equipment application 500 of some embodiments that may determine the preferred hearing ranges for patients. In some embodiments, the testing equipment application 500 is a stand-alone application or is integrated into another application, while in other embodiments the application might be implemented within an operating system 530. Furthermore, in some embodiments, the testing equipment application 500 is provided as part of a server-based solution or a cloud-based solution. In some such embodiments, the application is provided via a thin client. That is, the application runs on a server while a user interacts with the application via a separate machine remote from the server. In other such embodiments, the application is provided via a thick client. That is, the application is distributed from the server to the client machine and runs on the client machine.

The testing equipment application 500 includes a user interface (UI) interaction and generation module 502, management (user) interface tools 504, test procedure modules 506, frequency generator modules 508, decibels modules 510, notification/alert modules 512, report modules 514, database module 516, an operator module 518, and a health care professional module 520. The testing equipment application 500 has access to a testing equipment database 522, which in one embodiment, may include test procedure data 524, patient data 526, and presentation instructions 528. In some embodiments, storages 524, 526, 528 are all stored in one physical storage. In other embodiments, the storages 524, 526, 528 are in separate physical storages, or one of the storages is in one physical storage while the other is in a different physical storage.

The order of execution or performance of the methods and data flows illustrated and described herein is not essential, unless otherwise specified. That is, elements of the methods and data flows may be performed in any order, unless otherwise specified, and that the methods may include more or less elements than those disclosed herein. For example, it is contemplated that executing or performing a particular element before, contemporaneously with, or after another element are all possible sequences of execution.

While this invention has been described with reference to illustrative embodiments, this description is not intended to be construed in a limiting sense. Various modifications and combinations of the illustrative embodiments as well as other embodiments of the invention, will be apparent to persons skilled in the art upon reference to the description. It is, therefore, intended that the appended claims encompass any such modifications or embodiments.

What is claimed is:

1. A system for aiding hearing, the system comprising:
  a programming interface configured to communicate with a device, the device including a housing securing a speaker, a user interface, a processor, non-transitory memory, and storage therein, the device including a busing architecture communicatively interconnecting the speaker, the user interface, the processor, the memory, and the storage;
  the non-transitory memory accessible to the processor, the non-transitory memory including processor-executable instructions that, when executed, by the processor cause the system to:
    screen, via the speaker and the user interface, a left ear of a patient at an incrementally selected frequency between a frequency range of 50 Hz to 5,000 Hz at a first increment at a decibel range of 10 db to 120 db, with detected frequencies being re-ranged tested at a second increment, the second increment being more discrete than the first increment;
    screen, via the speaker and the user interface, the left ear of the patient at an incrementally selected frequency between a frequency range of 5,000 Hz to 10,000 Hz at a third increment at a decibel range of 10 dB to 120 dB, with detected frequencies to be re-range tested at a fourth increment, the fourth increment being more discrete than the third increment;
    determine a left ear preferred hearing range, the left ear preferred hearing range being a range of sound corresponding to highest hearing capacity of the left ear of the patient between 50 Hz and 10,000 Hz;
    screen, via the speaker and the user interface, a right ear of the patient at an incrementally selected frequency between a frequency range of 50 Hz to 5,000 Hz at the first increment at a decibel range of 10 db to 120 db, with detected frequencies being re-ranged tested at the second increment;
    screen, via the speaker and the user interface, the right ear of the patient at an incrementally selected frequency between a frequency range of 5,000 Hz to 10,000 Hz at the third increment at a decibel range of 10 dB to 120 dB, with detected frequencies to be re-range tested at the fourth increment; and
    determine a right ear preferred hearing range, the right ear preferred hearing range being a range of sound corresponding to highest hearing capacity of the right ear of the patient between 50 Hz and 10,000 Hz.

2. The system as recited in claim 1, wherein the right ear is screened prior to the left ear.

3. The system as recited in claim 1, wherein the left ear preferred hearing range and the right ear preferred hearing range are mutually exclusive.

4. The system as recited in claim 1, wherein the left ear preferred hearing range and the right ear preferred hearing range at least partially overlap.

5. The system as recited in claim 1, wherein the left ear preferred hearing range further comprises a plurality of narrow hearing ranges.

6. The system as recited in claim 1, wherein the right ear preferred hearing range further comprises a plurality of narrow hearing ranges.

7. The system as recited in claim 1, wherein the speaker further comprises a left speaker and a right speaker.

8. The system as recited in claim 7, wherein the left speaker and the right speaker are respectfully incorporated into a left and a right body connected by a band member, each of the left and the right bodies at least partially conforming to contours of an external ear and sized to engage therewith.

9. The system as recited in claim 1, wherein the device further comprises a smart device.

10. The system as recited in claim 1, wherein the smart device further comprises a device selected from the group consisting of smart watches, smart phones, and tablet computers.

11. The system as recited in claim 1, wherein the device further comprises a computer.

12. The system as recited in claim 1, wherein the device further comprises a headset hearing tester.

13. The system as recited in claim 1, wherein the processor executable instructions further comprise processor executable instructions that, when executed, cause the processor to utilize distributed processing between the device and a server to screen, via the speaker and the user interface, the left ear of the patient.

14. The system as recited in claim 1, wherein the processor executable instructions further comprise processor executable instructions that, when executed, cause the processor to utilize distributed processing between the device and a server to screen, via the speaker and the user interface, the right ear of the patient.

15. The system as recited in claim 1, wherein the processor executable instructions further comprise processor executable instructions that, when executed, cause the processor to utilize distributed processing between the device and a server to determine the left ear preferred hearing range.

16. The system as recited in claim 1, wherein the processor executable instructions further comprise processor executable instructions that, when executed, cause the processor to utilize distributed processing between the device and a server to determine the right ear preferred hearing range.

17. The system as recited in claim 1, wherein the processor executable instructions further comprise processor executable instructions that, when executed, cause the processor to execute hearing aid programming for each of the left ear and the right ear.

18. A system for aiding hearing, the system comprising:
a programming interface configured to communicate with a smart device, the smart device including a housing securing a speaker, a user interface, a processor, non-transitory memory, and storage therein, the device including a busing architecture communicatively interconnecting the speaker, the user interface, the processor, the memory, and the storage, the smart device being a device selected from the group consisting of smart watches, smart phones, and tablet computers;
the non-transitory memory accessible to the processor, the non-transitory memory including processor-executable instructions that, when executed, by the processor cause the system to:
screen, via the speaker and the user interface, a left ear of a patient at an incrementally selected frequency between a frequency range of 50 Hz to 5,000 Hz at 50 Hz increments at a decibel range of 10 db to 120 db, with detected frequencies being re-ranged tested at a 5 Hz to 20 Hz increment;
screen, via the speaker and the user interface, the left ear of the patient at an incrementally selected frequency between a frequency range of 5,000 Hz to 10,000 Hz at a first increment at a decibel range of 10 dB to 120 dB, with detected frequencies to be re-range tested at second increment to better identify the frequencies and decibel levels heard, the second increment being more discrete than the first increment;
determine a left ear preferred hearing range, the left ear preferred hearing range being a range of sound corresponding to highest hearing capacity of the left ear of the patient between 50 Hz and 10,000 Hz;
screen, via the speaker and the user interface, a right ear of the patient at an incrementally selected frequency between a frequency range of 50 Hz to 5,000 Hz at the first increment at a decibel range of 10 db to 120 db, with detected frequencies being re-ranged tested at the second increment;
screen, via the speaker and the user interface, the right ear of the patient at an incrementally selected frequency between a frequency range of 5,000 Hz to 10,000 Hz at a third increment at a decibel range of 10 dB to 120 dB, with detected frequencies to be re-range tested at a fourth increment to better identify the frequencies and decibel levels heard, the fourth increment being more discrete than the third increment; and
determine a right ear preferred hearing range, the right ear preferred hearing range being a range of sound corresponding to highest hearing capacity of the right ear of the patient between 50 Hz and 10,000 Hz.

19. The system as recited in claim 18, wherein the processor executable instructions further comprise processor executable instructions that, when executed, cause the processor to utilize distributed processing between the device and a server to at least one of screen the left ear, screen the right ear, determine the left ear preferred hearing range, and determine the right ear preferred hearing range.

20. A system for aiding hearing, the system comprising:
a programming interface configured to communicate with a device, the device including a housing securing a speaker, a user interface, a processor, non-transitory memory, and storage therein, the device including a busing architecture communicatively interconnecting the speaker, the user interface, the processor, the memory, and the storage;
the non-transitory memory accessible to the processor, the non-transitory memory including processor-executable instructions that, when executed, by the processor cause the system to:
screen, via the speaker and the user interface, a left ear of a patient at an incrementally selected frequency between a frequency range of 50 Hz to 5,000 Hz, with detected frequencies being re-ranged tested to better identify the frequencies and decibel levels heard;
screen, via the speaker and the user interface, the left ear of the patient at an incrementally selected frequency between a frequency range of 5,000 Hz to 10,000 Hz, with detected frequencies to be re-range tested to better identify the frequencies and decibel levels heard;
determine a left ear preferred hearing range, the left ear preferred hearing range being a range of sound corresponding to highest hearing capacity of the left ear of the patient between 50 Hz and 10,000 Hz;
screen, via the speaker and the user interface, a right ear of the patient at an incrementally selected frequency between a frequency range of 50 Hz to 5,000 Hz, with detected frequencies being re-ranged tested to better identify the frequencies and decibel levels heard;
screen, via the speaker and the user interface, the right ear of the patient at an incrementally selected frequency between a frequency range of 5,000 Hz to 10,000 Hz, with detected frequencies to be re-range tested to better identify the frequencies and decibel levels heard; and determine a right ear preferred hearing range, the right ear preferred hearing range being a range of sound corresponding to highest hearing capacity of the right ear of the patient between 50 Hz and 10,000 Hz.

* * * * *